United States Patent [19]

Long

[11] 4,309,617
[45] Jan. 5, 1982

[54] PULSED RADIATION SOURCE ADAPTED FOR CURING DENTAL RESTORATIVES

[75] Inventor: William H. Long, Woodbury, Minn.

[73] Assignee: Minnesota Mining and Manufacturing Company, Saint Paul, Minn.

[21] Appl. No.: 172,019

[22] Filed: Jul. 24, 1980

Related U.S. Application Data

[63] Continuation-in-part of Ser. No. 17,805, Mar. 5, 1979, abandoned.

[51] Int. Cl.³ ............................................. G01J 1/00
[52] U.S. Cl. ............................................. 250/504 H
[58] Field of Search ............ 433/32; 250/503, 504 R, 250/504 H, 453, 505; 313/110, 113

[56] References Cited

U.S. PATENT DOCUMENTS

| | | | |
|---|---|---|---|
| 3,712,984 | 1/1973 | Lienhard | 250/504 H |
| 3,868,513 | 2/1975 | Gonser | 250/504 H |
| 4,009,382 | 2/1977 | Nath | 240/1 LP |
| 4,229,658 | 10/1980 | Gonser | 250/504 H |

FOREIGN PATENT DOCUMENTS 2711962 10/1977 Fed. Rep. of Germany .
2305092 11/1976 France .

Primary Examiner—Bruce C. Anderson
Attorney, Agent, or Firm—Cruzan Alexander; Donald M. Sell; William B. Barte

[57] ABSTRACT

An apparatus for providing controlled flashes of radiation, including a handpiece within which is mounted a gaseous discharge tube and a light pipe for conducting the radiation, enabling it to be directed into an oral cavity to effect in situ curing of radiation polymerizable resins used as dental restoratives. The apparatus further includes electrical circuitry for producing a train of a fixed number of relatively constant intensity flashes each time a switch is closed, and for disabling the apparatus after the flash tube has been discharged a predetermined number of times, thereby preventing unsatisfactory performance resulting from a fall-off in intensity due to aging of the tube.

15 Claims, 4 Drawing Figures

4,309,617

PULSED RADIATION SOURCE ADAPTED FOR CURING DENTAL RESTORATIVES

This is a continuation-in-part application of Ser. No. 17,805, filed Mar. 5, 1979 abandoned.

BACKGROUND OF THE INVENTION

1. Field of the Invention

This invention relates to apparatus for providing pulsed energization of gaseous discharge tubes and in particular, to the use of such radiation produced thereby in the in situ curing (e.g., polymerization) of small quantities of synthetic resins such as may be used as dental restoratives.

2. Description of the Prior Art

The use of UV radiation for curing synthetic resins is well recognized, and has been heretofore exploited in a variety of applications. Due to the limitations of the intensity and energy densities of typical UV sources, including the sun, such applications have primarily been directed to systems where relatively long cure times are practical, i.e., typically on the order of hours or significant fractions thereof.

Nonetheless, where the amounts of resin to be cured are sufficiently small, attempts have been made in the past to direct UV radiation onto such amounts to effect in situ cure even where very rapid curing is required, such as where it is virtually impossible to maintain the physical placement and environment proximate the resin constant for more than a few seconds.

One such application area lies in the field of dental restoratives, in which a synthetic resin composition having a putty-like consistency is inserted into cavities of teeth and is cured in situ to form strong fillings and coatings. In another application, a much more fluid composition, for example, in the range of several hundred centipoises, may be applied as a surface coating to occlusive surfaces to fill in pits and fissures, whereupon the coating is cured in a similar fashion. A major problem in effecting such in situ UV curing of dental resins lies in the difficulty in directing an appropriate quantity of radiation suitable for such curing into the location of the resin in a fashion which is acceptable from technological, convenience, and patient safety viewpoints.

For example, as depicted in French Pat. No. 2,305,092, issued on Mar. 19, 1976, to Donald Allan Gonser, one proposed device for such an application includes a super-atmospheric non-confined Xenon arc lamp which is enclosed in housing adapted to be hand held, and to which is fitted a quartz rod for conducting UV light from the source into an oral cavity. The device further includes electrical circuitry which is desirably located in a remote enclosure for generating electrical pulses which are coupled to the lamp via a coaxial cable. Such a device is said to optimize the production of desirable radiation, i.e., that within the 320-390 nm range, while minimizing the amount of heat produced. However, it has been found that a configuration such as there described is limited in the luminous intensity which can be directed onto a dental filling, as well as in the lack of control over the uniformity in intensity between successive flashes, depending upon operating voltages and history of the flash lamp.

Another device intended for similar applications is depicted in German Pat. No. 2,711,962 (Buzzi et al). In that publication, rechargeable Xe flash tubes, together with quartz rods, are also depicted, as is the suggestion of some form of switching arrangement permitting control over the number of flashes for a given curing requirement. Likewise, no provision is suggested for increasing the luminous intensity or for controlling the uniformity of the intensity of successive flashes.

Also, U.S. Pat. No. 4,009,382 (Nath) depicts apparatus intended for similar applications, but in which radiation is coupled to the patient's mouth by means of a UV transmissive, liquid filled channel.

SUMMARY OF THE INVENTION

The apparatus of the present invention bears certain similarities to that depicted in the references noted above in that it includes a housing adapted to be hand-held proximate an oral cavity, a gaseous discharge tube positioned within the housing for providing a source of radiation, a radiation transmissive rod for coupling radiation from the tube and through the housing, said rod being adapted for insertion into an oral cavity to direct said radiation toward a radiation polymerizable composition therein, and a power supply for intermittent energization of the tube. Because it has now been found desirable to be able to cure both UV curable compositions and similar curable compositions which respond to radiation at other wavelengths, such as visible light, etc., then the discharge tube and transmission rod used in the apparatus of the present invention are selected to provide radiation at wavelengths appropriate to the compositions to be used therewith.

In addition to such components, and in further definition thereof, in one embodiment, the apparatus of the present invention is characterized by a power supply which includes components for ensuring controlled energization of the discharge tube. Accordingly, the supply includes control means for applying a predetermined potential to the charge storage means during quiescent periods during which the discharge tube is unenergized. The supply also includes hold-off means coupled to the control means for preventing the application of potential to the charge storage means for at least a predetermined duration following each energization of the discharge tube, pulse control means for generating a train of a predetermined number of electrical pulses within a given interval of time, and means for coupling the pulse train to trigger means associated with the discharge tube in response to an initiate signal. Such a pulse train thus causes the discharge tube to be energized a like number of times for each occurrence of an initiate signal. The control means ensures that a constant amount of energy is stored in the charge storage means between each flash such that each flash has associated therewith a substantially constant amount of energy. To further ensure satisfaction with the performance of the apparatus, the supply also includes means for providing an indication when the intensity of successive flashes produced upon the discharge of the constant amount of energy into the tube decreases to a predetermined minimum level. The desirability of replacing the discharge tube is thus indicated prior to the onset of unsatisfactory curing of typical amounts of the polymerizable compositions due to a fall-off in the intensity. One such indication providing means is desirably a counter circuit which is responsive to provide an indication where the number of pulses coupled to trigger the discharge tube exceeds a predetermined number. Since the intensity of flashes produced under controlled applications is a readily determinable function of the number of flashes, such a count is conveniently utilized as an indication of relative intensity.

In another embodiment, the apparatus of the present invention includes a handpiece comprising a housing, a radiation producing gaseous discharge tube and a radiation transmissive rod such as described above, together with a power supply for intermittent energization of the tube, in which the handpiece is characterized by a preferred assembly for ensuring efficient coupling of radiation emitted by the tube into the rod. In this embodiment, the transmissive rod includes a light pipe having a lower index cladding layer surrounding a higher index core, and the handpiece includes means for receiving an end of the rod into the housing such that the end is butted against a first surface of the tube, reflector means positioned within said housing having a generally concave and reflecting surface for receiving the tube therein such that the first surface of the tube may be butted against said received end of the rod, thus also redirecting radiation emitted from said tube toward the received end of said rod, and mechanical bias means for maintaining the rod, tube, and reflector means in a butted-together relationship in intimate optical contact so as to maximize the collection of emitted radiation within the light pipe and thence toward the composition to be cured.

DESCRIPTION OF THE PREFERRED EMBODIMENTS

Figure 1:
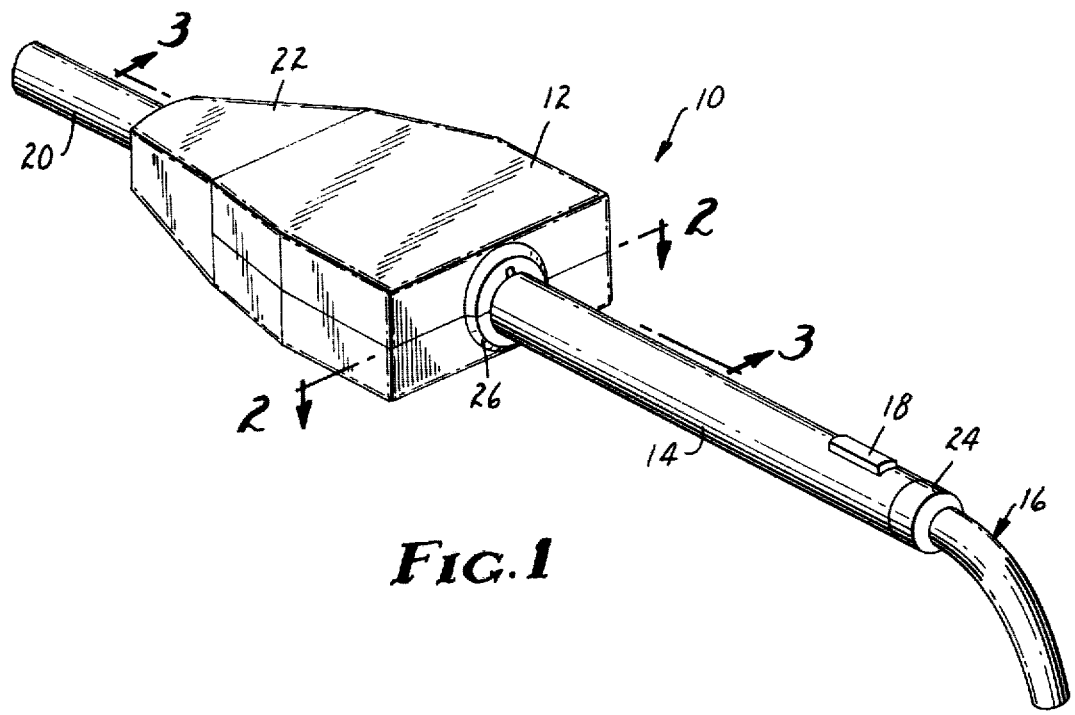
FIG. 1 is a three dimensional view of the handpiece of the apparatus of the present invention.

As shown in FIG. 1, the preferred embodiment of a handpiece 10, for use with the apparatus of the present invention, includes a housing 12, within which are mounted a gaseous discharge flash tube (not shown) together with certain additional components, all of which are described in more detail hereinafter. The handpiece 10 further includes an extension 14 within which is mounted a radiation-transmissive light pipe 16 including a rod of fused quartz. This pipe 16 extends through the extension 14 and directs light from the flash tube within the housing 12 into an oral cavity as desired. Also mounted on the extension 14 is a switch 18 which when closed provides a signal to initiate a train of flashes of radiation. In order that the handpiece be as light and convenient to use as possible, most of the electrical components required for producing the desired flashes of radiation are included in a separate electronic module connected to the handpiece 10 by means of a cable 20. Such a cable is desirably connected to the housing 12 by means of a connector 22.

To further enhance the utility of the apparatus for curing polymerizable resins such as may be used for dental restoratives within an oral cavity, the light pipe 16 is desirably secured to the extension 14 by means of a twist-lock collet 24, such that the pipe 16 may be readily removed for separate sterilization and/or replacement, aand reinserted at any angle of rotation with respect to the housing 12 by merely unlocking the collet 4. Similarly, the entire extension 14, as well as the light pipe 16, may be removed from the housing 12 by means of a conventional bayonet mounting 26, thus allowing the entire extension to be removed for sterilization or replacement, or the like.

Figure 2:
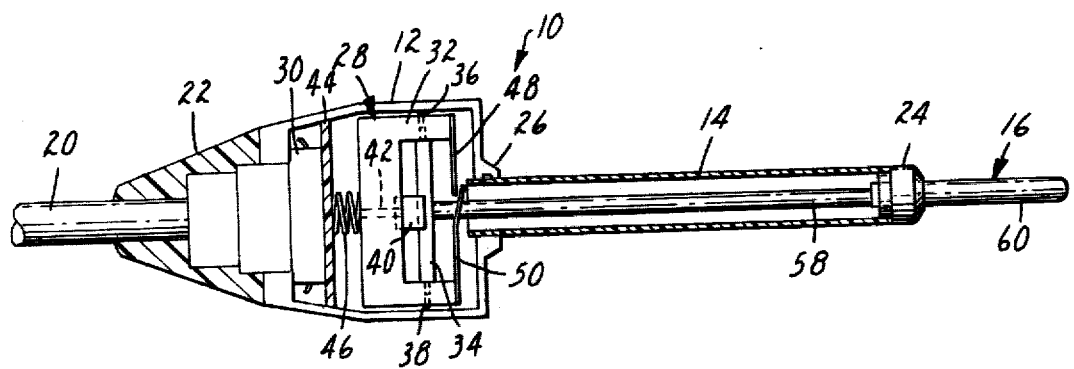
FIG. 2 is a cross-sectional view, taken along a line 2—2 of the handpiece shown in FIG. 1.

As shown in more detail in FIG. 2, the housing 12 includes a cavity within which are mounted a flash tube assembly 28 and a trigger pulse transformer 30. The flashtube assembly 28 is there seen to include a mounting yoke 32 having a front opening portion within which a tubular, gaseous discharge tube 34 is positioned. Electrodes, 36 and 38 respectively, extending from each end of the tube 34 are received into slots on the yoke 32 within which are positioned spring loaded contacts (not shown). Insulated wires (also not shown) connect the contacts within the yoke 32 to the connector 22. The tube assembly 28 also includes a reflector 40 which is mounted within a recess on the yoke 32 by means of a screw 42. The entire assembly 32 is biased away from a rear wall 44 by means of a coil spring 46, thus keeping the leading edge of the lamp 34 abutted against the light pipe 16 when it is inserted into the housing 12. The reflector 40 is desirably formed of a stainless steel or like conductive material. Electrical contact from the trigger transformer 30 is made through the screw 42 to the reflector 38, thereby enabling the reflector to serve as a trigger electrode for the tube 34. Also shown in FIG. 2 is a switch formed from two leaf spring members 48 and 50 respectively. These members are in turn wired to the connector 22, and when shorted together, such as by movement of the push button 18, shown in FIG. 1, provides a signal which initiates operation of the discharge tube.

Figure 3:
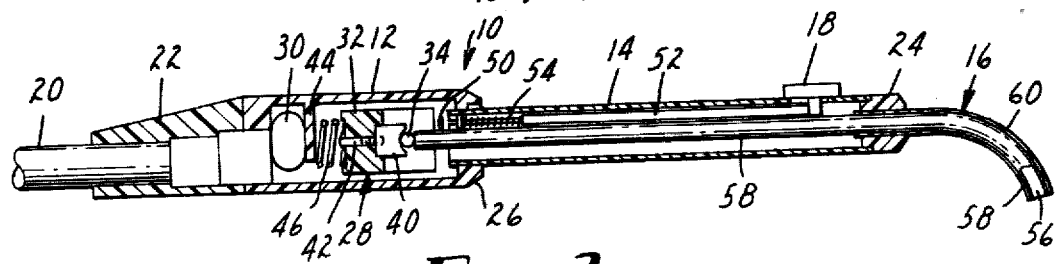
FIG. 3 is a cross-sectional side view taken along a line 3—3 of the handpiece shown in FIG. 1.

As further shown in FIG. 3, the closure of the switch elements 48 and 50 is desirably effected by the button 18 via a linked push rod 52 which is in turn biased by a coil spring 54 against the spring element 50, such that when the button 18 is moved, contact between the elements 50 and 48 is effected. Also clearly shown in FIG. 3 is the relative placement of the flash tube 34 between the reflector 38 and the rear face of the light pipe 16 such that those members are maintained butted against each other, thus maximizing the collection of radiation emitted from the flash tube 34 into the light pipe 16. As is seen in the right hand portion of FIG. 3, the light pipe 16 desirably comprises a quartz rod 56, an inner cladding layer of a low index of refraction material such as polytetrafluoroethylene, and an outer, opaque cladding layer 60, such as black vinyl. The inner, low index cladding layer 58 causes light to be inwardly reflected, enabling the quartz rod 56 to act as a light pipe, while the outer black layer 60 prevents light from escaping through the side of the rod so as to avoid potential glare to the operator of the apparatus.

Figure 4:
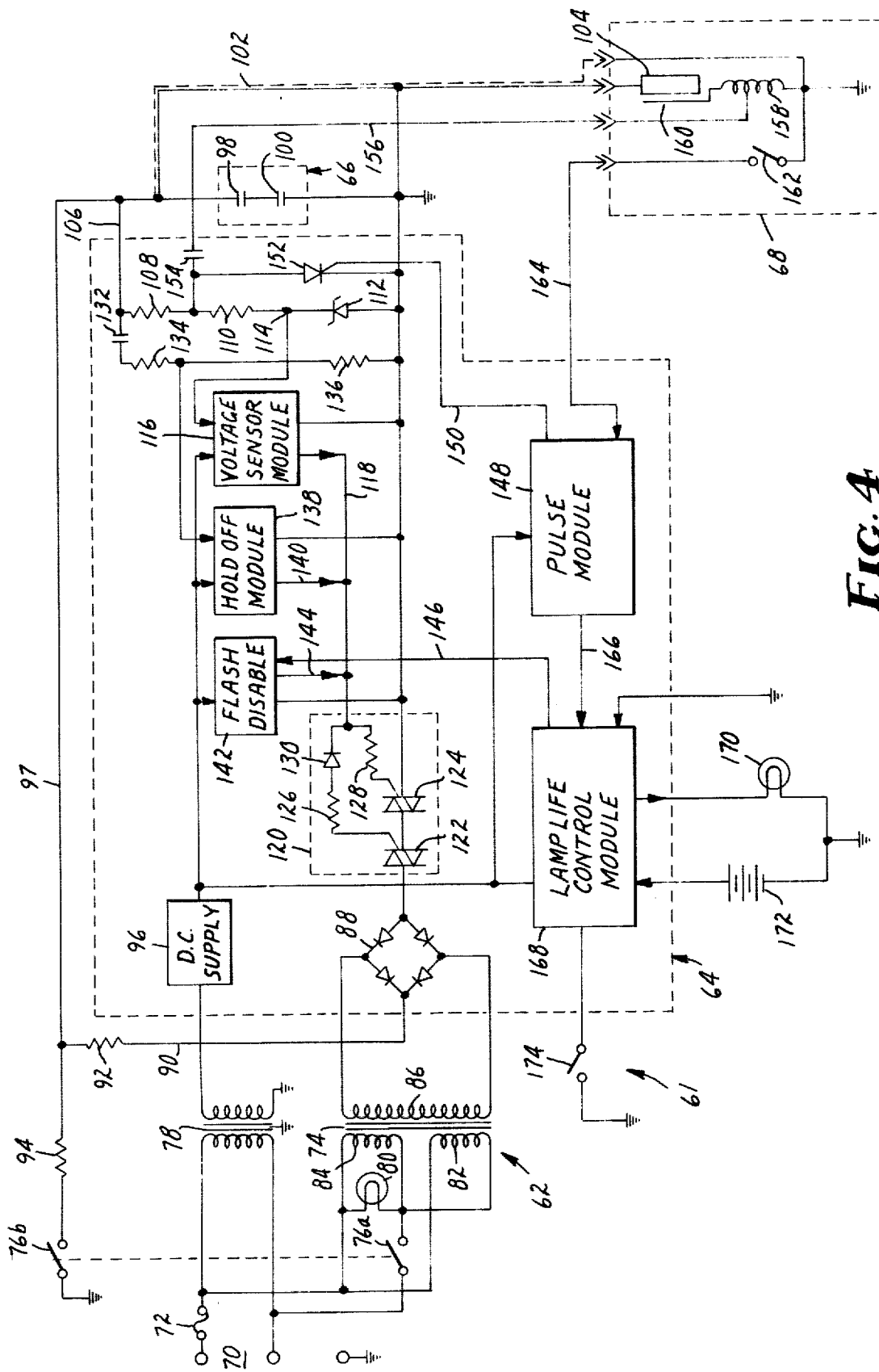
FIG. 4 is a circuit diagram of a preferred circuit of the apparatus of the present invention.

As shown in FIG. 4, a preferred circuit 61 for use in the apparatus of the present invention includes an input power section 62, a control module 64, a charge storage section 66, and the handpiece section 68. The input power section 62 includes terminals 70 at which either 110 or 220 VAC, at 50 or 60 Hz may be supplied to the apparatus. This power is coupled through an input fuse 72 and one section of an on/off switch 76a to a primary power transformer 74. The input power through the fuse 72 is also coupled to a supplemental transformer 78. The application of power through the switch 76a is indicated by means of pilot light 80. The transformer 74 is provided with a pair of primary windings 82 and 84 which may be connected in series or in parallel, depending upon the input power being supplied. The secondary winding 86 of the transformer 74 is coupled into the control module 64 to a diode bridge rectifier 88. As a result of the rectifying action of the bridge rectifier 88, a positive 450 VDC potential is caused to appear on lead 90, and is coupled through resistor 92 to a DC supply line 97. The DC power is discharged through resistor 94 and the second half of the on/off switch 76b when the apparatus is turned off. The on/off switch 76a and 76b is desirably mounted within a cradle secured to the electronic module, adapted to receive the handpiece 10 shown in FIGS. 1 through 3. Thus, when the handpiece is returned to the cradle, the primary DC potential is automatically withdrawn from the apparatus. The output from the supplemental transformer 78 is coupled into the control module 64 to a secondary DC power 96 to provide a source of DC potential for the low voltage portions of the circuit.

The DC potential appearing on lead 97 is coupled to the charge storage section 66, which comprises a bank of two capacitors 98 and 100, respectively in series, and through a shielded cable 102 to a gaseous discharge tube 104 located within the handpiece 68. Power from the DC bus 97 is also coupled as an input control signal 94 via lead 106 into the control module 64, to enable sensing of the potential such that regulation of the potential may be effected. This control function is accomplished by means of a voltage divider including resistors 108 and 110, together with a Zener diode 112. The Zener diode establishes an absolute reference potential of 7.0 VDC at node 114, and provides a signal to the voltage sensor module 116 whenever the potential on lead 106 rises above a predetermined level such that the Zener diode 112 begins to conduct. The module 116 operates on the signal from node 114, and provides an ouptut on lead 118 which is coupled to a voltage control network 120. The network 120 comprises two Triacs 122 and 124, which are wired in series in the ground current return path to the bridge rectifier 88. The conductances of the respective Triacs 122 and 124 are, in turn, controlled through resistors 122 and 128, together with diode 130 in response to the control signal on lead 118. Thus, when the control signal on lead 118 rises or falls, as appropriate, the conductance of the Triacs 122 and 124 is adjusted so as to modify the relative level of the high voltage, thereby maintaining the potential appearing across capacitors 98 and 100 at a constant level.

The input control signal appearing on lead 106 is also coupled through capacitor 132 to a voltage divider comprising resistors 134 and 136. A proportionate voltage appearing therebetween is coupled to the hold-off module 138. The RC network formed from components 132, 134 and 136 responds to a momentary drop in potential at lead 106 due to the discharge of capacitors 98 and 100 into the flash tube 104 and provides an inhibit signal, the duration of which is controlled by the relative values of those components. Upon appearance of such a signal, the holdoff module 138 provides a control signal on lead 140 which prevents the Triacs 122 and 124 within the voltage control module 120 from conducting for a predetermined period, such as for example approximately 50 milliseconds. This prevents the capacitors 98 and 100 from being charged during this period and ensures extinction of the flash tube 104 between successive flashes.

A final input control to the voltage control module 120 is provided from the flash disable module 142 via lead 144 and similarly prevents the Triacs 122 and 124 from conducting in response to the occurrence of an input signal on lead 146 as described hereinafter.

The basic electrical control over the discharge of the flash tube 104 is provided via a pulse module 148. This module includes conventional pulse circuits for generating a train of a predetermined number of electrical pulses within a predetermined interval of time, which train is coupled via lead 150 to a trigger circuit including SCR 152 and capicator 154. In a preferred embodiment, the module 148 includes a free running oscillator which generates pulses of a few microseconds duration every one-half second. The module 148 further includes a gate which opens for a five second period in response to an initiate signal on lead 164 thereby allowing a train of ten pulses to be coupled on lead 150. Upon the occurrence of such a signal on lead 150, the SCR 152 is caused to conduct, thereby discharging capacitor 154. This in turn provides a pulse on lead 156 which is coupled into the handpiece 68 to the input of a pulse transformer 158. The output of the transformer 158 is coupled to a trigger electrode 160 associated with the flash tube 104. As shown in FIGS. 2 and 3, such an electrode may be the reflector member 38. Accordingly, the occurrence of an electrical pulse on lead 150 causes the application of a high voltage (7 KV) pulse on electrode 160 such as to reduce the hold-off voltage within the flash tube 104, which in turn causes the discharge of the capacitor 98 and 100 through the flash tube, thereby providing a flash of light, the duration of which is controlled by the time constants associated with the capacitors 98 and 100, the discharge tube 104 and the cable therebetween. Accordingly, the duration of the light flashes provided by the discharge tube 104 are approximately 0.5 milliseconds in duration. A switch 162, the operation of which is controlled by movement of the button 18 on the handpiece shown in FIG. 1, may be seen in FIG. 4 to provide an initiate signal on lead 164 which is coupled to the pulse module 148, causing the circuit and associate components therewithin to provide the train of pulses on lead 150.

It has been found that the degree of hardness produced in a predetermined amount of UV polymerizable resin by the train of 10 flashes from the flash tube 104 when discharged under constant potential conditions is essentially a linear function of the lifetime of the flash tube, i.e., the number of times the tube has been flashed. Accordingly, the onset of unsatisfactory curing may be indicated by monitoring the number of times the tube has been discharged. Such a monitoring operation is performed by the lamp life control module 168. The module is responsive to an input signal from the pulse module 148, which occurs each time a trigger pulse is produced on lead 150. The module 168 includes a counter responsive to the total number of flashes and provides an output signal on lead 146 to disable subsequent charging of the charge storage means when the number of such pulses exceeds a predetermined value. At such a time the module 168 also provides a visual indication by means of a pilot light 170. A standby power supply 172 is also coupled to the control module 168 so as to ensure the retention of the running count regardless of the loss of input power on terminal 70. The module 168 is reset upon closure of reset switch 174, and replacement of the handpiece into the cradle, thereby opening the on/off switch 76. A further interlock also is provided, such that the control module 168 cannot be reset until the connector (22, FIGS. 1-3) between the cable and the handpiece 68 is disconnected.

The handpiece is desirably constructed so as to require such a disconnection before the housing to the handpiece can be opened in order to enable lamp replacement. This interlock feature thus ensures replacement of the lamp prior to further use of the apparatus.

Having now described the general features of the circuit shown in FIG. 4, the operation of the apparatus may readily been seen to include the following series of steps:

Upon removal of the handpiece 68 from a platform associated with the electric module, switch 76 is closed, causing power on input terminals 70 to be applied to the transformers 74 and 78. At the same time, the short circuit through switch 76b is removed, allowing 450 VDC to be applied along the bus 97. This energizes the high voltage portion of the apparatus, allowing operation of the flash tube. The operation of the tube itself is initiated upon the depression of switch 162 within the handpiece 68. This grounds the input to the pulse module 148 and activates a series of 10 pulses spaced approximately one-half second apart, which are coupled to the input of the SCR 152. These pulses in turn activate the SCR 152, causing the capacitor 154 to discharge to ground. A pulse is thereby provided which is coupled to the pulse transformer 158, and which is amplified to provide an approximate 7 KV pulse on the trigger 160, thereby reducing the hold-off voltage within the tube 104. This in turn causes the discharge of the capacitors 98 and 100, to provide the light flashes. After such discharge, the RC network comprising components 132, 134 and 136 provides an approximately 50 millisecond pulse which is coupled to the hold-off module 138, and thereby prevents the recharging of capacitors 98 and 100 for a like period, thereby ensuring the extinction of the arc within the flash tube 104 between successive flashes.

Successive series of flashes for additional restorations are obtained simply by successive closures of switch 162. When the total number of such restorations has exceeded a predetermined number, the total count from the pulse module as coupled to the lamp life control module 168 causes a disable signal to be provided on lead 146 to the flash disable module 142, thereby preventing further recharging of the capacitors 98 and 100.

Resetting of the module 168, as discussed hereinabove, is enabled by a closure of the reset switch 174 and the appropriate operation of the interlock feature.

A typical example indicative of the manner in which the onset of unsatisfactory curing occurs as a function of the number of times the flash tube is discharged is represented in Table I, wherein a succession of tests using flashes of UV were performed on a UV curable dimethacrylate resin loaded with ca. 82% powdered quartz together with a photoinitiator such as "Irgacure" type 651, manufactured by Ciba-Geigy Corp., a benzil dimethylketal type catalyst.

TABLE I

| No. of Restorations | Hardness Top | Hardness Bottom |
|---|---|---|
| 1 | 84 | 75 |
| 300 | 80 | 75 |
| 600 | 80 | 75 |
| 800 | 78 | 68 |
| 1000 | 75 | 66 |
| 1200 | 75 | 62 |
| 1400 | 72 | 50 |

In the data there shown, a single restoration is defined as being a series of 10 flashes over a 5-second interval in which the flashes are directed onto a pellet of UV curable resin approximately 6 millimeters in diameter and 1.5 millimeters thick. The resultant curing is then determined using a Barber-Colman Impressor Model GYZJ 934-1. As is shown in the Table, the hardness of the top and the bottom of the pellet after exposure to the series of flashes exceeds a relative hardness level of 75 when the flash tube is first operated. After approximately 1,000 such restorations, the bottom hardness is observed to decrease to a relative level of approximately 65. A relative bottom hardness level associated with satisfactory performance has been found to be approximately 65. In order to provide an adequate margin of safety, the control module 168 has accordingly been designed to provide a disable signal when 600 restorations, i.e., 6000 flashes has been counted. The module is readily modified to provide for a different desired count, depending upon an emperic determination of the lifetime characterics of the discharge tube as used in a particular discharge circuit.

In the preferred embodiment discussed above, the circuit shown in FIG. 4 is designed with components having the following electrical characteristics:

TABLE II

| Capacitors | Resistors | Miscellaneous | |
|---|---|---|---|
| 98, 400 fd, 330V | 92 150 ohm, 20 wt. | 72 | fuse, 2 amp. |
| 100 400 fd, 330V | 94 350 ohm | 74 | Primary Transformer; 110/220 Primary |
| 132 0.02 fd,600V | 108 330 Kohm, ½wt. | | |
| 154 0.0068 fd, 400V | 110 330 Kohm, ½wt. | | 400 VAC secondary |
| | 126 270 ohm | 78 | Supplemental Transformer; |
| | 128 330 ohm | | 10 VAC secondary |
| | 134 1 Mohm, ½wt. | | |
| | 136 10 Kohm, ½wt. | 88 | diode bridge 1/5A 800V |
| | | 96 | Conventional DC Supply, 6.2 VDC |
| | | 104 | Flash tube FT-20-25U |
| | | 112 | Zener diode 7.0 V |
| | | 122 | TRIAC Hudson T106D2SG |
| | | 124 | TRIAC Hudson T106D2SG |
| | | 152 | SCR Hudson S1C |
| | | 158 | Pulse Transformer Schott Corp. 67077750 |
| | | 172 | 3.6 VDC Ni-Cd Battery, 70 MAH |

In another preferred embodiment, the apparatus of the present invention may also be utilized for curing synthetic resins susceptible to activation by visible light, particularly that of relatively short wavelengths, such as in the 400–500 nm range. In such an embodiment, it has been found desirable to modify the pulse module 148 and voltage sensor module 116 shown in FIG. 4 to provide a succession of flashes of reduced intensity, each flash occurring at 0.1 second intervals, and extending for 10–20 seconds, depending upon the desired exposure time and intensity.

A particularly suitable composition which may be cured with such flashes of visible light is a synthetic urethane dimethacrylate resin marketed by Johnson & Johnson Dental Products Company, as "Fotofil" Brand Dental Restorative Resin. In tests involving such resin, satisfactory in situ curing of typical amounts (i.e., 6 mm diameter ×1.5 mm thick pellets) utilized in average dental restorations has been found to result in similar hardness values as that noted above for UV cured resins when tested in the same manner.

While the electrical and mechnical characteristics of the various components as described hereinabove are preferred, it is similarly recognized that a variety of alternatives are similarly within the scope of the present invention. For example, the handpiece 68 may be designed as a pistollette or as a tubular configuration, and may include varying numbers of electrical components, depending upon weight and miniaturization considerations. Similarly, the electrical circuit shown in FIG. 4 may be modified as known to those skilled in the art, including the use of various types of flash tubes and appropriate modification of the charge storage means and/or trigger circuits depending upon the characteristics of the particular flash tube selected. Type FT-20-25U flash tubes as manufactured by the General Electric Company for industrial high intensity flash applications are preferred for both UV and visible light curing applications as that type tube produces a near continuum of energy extending from the UV through the IR spectrum.

Having thus described the present invention, what is claimed is:

1. Apparatus adapted for hardening radiation polymerizable compositions used in making dental restorations, said apparatus comprising
   a housing adapted to be hand-held proximate an oral cavity,
   a gaseous discharge tube mounted within the housing for providing a source of radiation,
   a radiation transmissive rod for coupling radiation from said tube and through the housing, said rod being adapted for insertion into an oral cavity to direct said radiation toward a said composition, and
   a power supply including charge storage means for intermittent energization of said tube,
   characterized by
   said power supply including
   (i) control means for applying a predetermined potential to said charge storage means during quiescent periods during which said discharge tube is unenergized,
   (ii) hold-off means coupled to said control means for preventing said application of potential to said charge storage means for at least a predetermined duration following each energization of said discharge tube,
   (iii) pulse control means for generating a train of a predetermined number of electrical pulses within a given interval of time, and for coupling said pulse train to trigger means associated with said discharge tube in response to an initiate signal to cause said discharge tube to be discharged a like number of times, each flash having associated therewith a substantially constant energy as controlled by said predetermined potential from said control means, and
   (iv) means for providing an indication when the intensity of successive flashes produced upon the discharge of said substantially constant amount of energy into the tube decreases to a predetermined minimum level, said indication providing means comprising counter means responsive to said pulse control means for representing the number of pulses coupled to said trigger means and for providing an indication when said number exceeds a predetermined value, such that the desirability of replacing said discharge tube is indicated prior to the onset of unsatisfactory curing of said compositions due to a fall-off in said intensity.

2. An apparatus according to claim 1, further comprising switch means positioned within said housing to be manually activated, and coupled to said pulse control means for providing a said intiate signal.

3. An apparatus according to claim 1, wherein said control means includes regulation means for maintaining the potential applied to said charge storage means at a substantially constant level.

4. An apparatus according to claim 1, wherein said hold-off means comprises means for disconnecting a ground path for said charge storage means, and timer means for controlling the disconnect period for said predetermined duration.

5. An apparatus according to claim 1, wherein said pulse control means comprises means for generating a train of pulses at predetermined intervals.

6. An apparatus according to claim 1 wherein said indication providing means further comprises means responsive to said indication for preventing application of potential to said charge storage means until said counter means is reset.

7. Apparatus adapted for hardening radiation polymerizable compositions used in making dental restorations, said apparatus comprising
   (a) a handpiece adapted to be hand-held proximate an oral cavity, including
   an exterior, UV radiation impermeable housing,
   a gaseous discharge tube mounted within said housing for providing a source of radiation, and
   a radiation transmissive rod optically coupled to said tube for conducting radiation from the tube and through the housing, said rod being adapted for insertion into an oral cavity to direct said radiation toward a said composition, and
   (b) a power supply for intermittent energization of said tube,
   characterized by
   said rod including a light pipe having a lower index cladding layer surrounding a higher index core,
   said handpiece including means for receiving an end of said rod into said housing such that said end is butted against a first surface of said tube, reflector means positioned within said housing having a generally concave, reflecting surface for receiving said tube therein such that said first surface of said tube may be butted against said received end of said rod and for redirecting radiation emitted from said tube toward said end of said rod, and mechanical bias means for maintaining said rod, tube, and reflector means in a butted-together relationship in intimate optical contact so as to maximum the collection of emitted radiation within the light pipe and thence toward a said composition.

8. An apparatus according to claim 7, wherein said housing includes means for allowing ready removal and reinsertion of said rod into said abutting relationship, such that said rod may be removed to permit sterilization thereof.

9. An apparatus according to claim 7, wherein said hand piece further comprises switch means positioned within said housing adapted for manual activation, and coupled to said pulse control means for providing a said initiate signal.

10. An apparatus according to claim 7, wherein said tube consists of a confined arc type tube having a substantially cylindrical envelope with cathode and anode electrodes sealed within opposite ends thereof and a substantially electrically conductive envelope portion electrically coupled to an electrically conductive portion of said reflector means such that an electrical trigger signal may be coupled therethrough to cause discharge of said tube.

11. An apparatus according to claim 7, wherein said power supply includes (a) charge storage means coupled to said source,
(b) control means for applying a predetermined potential to said charge storage means during quiescent periods during which said source is unenergized,
(c) hold-off means coupled to said control means for preventing said application of potential to said charge storage means for at least a predetermined duration following each energization of said discharge tube,
(d) pulse control means for generating a train of a predetermined number of electrical pulses within a given interval of time, and for coupling said pulse train to trigger means associated with said discharge tube in response to an initiate signal to cause said discharge tube to be discharged a like number of times, each flash having associated therewith a substantially constant energy as controlled by said predetermined potential from said control means, and
(e) means for providing an indication when the intensity of successive flashes produced upon the discharge of said substantially constant amount of energy into the lamp decreases to a predetermined minimum level, such that the desirability of replacing said discharge tube is indicated prior to the onset of unsatisfactory curing of said compositions due to a fall-off in said intensity.

12. An apparatus according to claim 11, wherein said control means includes regulation means for maintaining the potential applied to said charge storage means at a substantially constant level.

13. An apparatus according to claim 11, wherein said hold-off means comprises means for disconnecting a ground path for said charge storage means, and timer means for controlling the disconnect period for said predetermined duration.

14. An apparatus according to claim 11, wherein said indication providing means comprises counter means responsive to said pulse control means for representing the number of pulses coupled to said trigger means and for providing an indication when said number exceeds a predetermined value.

15. An apparatus according to claim 14 wherein said indication providing means further comprises means responsive to said indication for preventing application of potential to said charge storage means, until said counter means is reset.

* * * * *